(12) United States Patent
Pacholik et al.

(10) Patent No.: US 11,647,955 B2
(45) Date of Patent: May 16, 2023

(54) SURFACE ELECTRODE HAVING A MOUNTING ELEMENT FOR A MAGNETIC SENSOR

(71) Applicant: Vanguard AG, Berlin (DE)

(72) Inventors: Alexander Pacholik, Berlin (DE); Thomas Gutzmer, Berlin (DE); Martin Bilz, Michendorf (DE); Hagen Thielecke, Neuenhagen (DE); Ralf Kühner, Stuttgart (DE)

(73) Assignee: Vanguard AG, Berlin (DE)

( * ) Notice: Subject to any disclaimer, the term of this patent is extended or adjusted under 35 U.S.C. 154(b) by 879 days.

(21) Appl. No.: 16/456,487

(22) Filed: Jun. 28, 2019

(65) Prior Publication Data

US 2020/0000407 A1 Jan. 2, 2020

(30) Foreign Application Priority Data

Jun. 29, 2018 (DE) ...................... 10 2018 115 812.2

(51) Int. Cl.
*A61B 5/00* (2006.01)
*A61B 5/0522* (2021.01)

(52) U.S. Cl.
CPC .......... *A61B 5/6833* (2013.01); *A61B 5/0002* (2013.01); *A61B 5/0522* (2013.01)

(58) Field of Classification Search
CPC .... A61B 2560/0406; A61B 2560/0443; A61B 2562/16; A61B 2562/164; A61B 2562/18;

(Continued)

(56) References Cited

U.S. PATENT DOCUMENTS

| | | | |
|---|---|---|---|
| 2005/0090759 A1* | 4/2005 | Borgmeier | A61B 5/4869 216/13 |
| 2007/0073129 A1* | 3/2007 | Shah | A61B 5/6849 600/347 |

(Continued)

FOREIGN PATENT DOCUMENTS

| | | |
|---|---|---|
| EP | 2389860 A1 | 11/2011 |
| EP | 2520223 A1 | 11/2012 |
| EP | 3586735 B1 | 8/2021 |

*Primary Examiner* — Thien M Le
(74) *Attorney, Agent, or Firm* — Tucker Ellis LLP; Michael G. Craig (57) ABSTRACT

A mounting element (8) for releasably receiving a sensor (18) for transferring and/or receiving electrical currents and/or signals relating to a body of an organism, comprising a mounting element base (9) having a receiving space (17) for receiving the sensor (18), the receiving space (17) comprising a floor (19), a wall (16) disposed on the floor (19) and disposed on at least three sides, an opening (20) formed by at least one tab (21, 22), at least one clip closure (23, 24), and further comprising a cover (10) for the mounting element base (9), an at least three-sided wall being disposed on the inner side (11) thereof, the end face (30) thereof being implemented for contacting the end face (41) of the wall (16), wherein at least one counterpart (28, 29) to the at least one clip closure (23, 24) is disposed on the wall (27), and the mounting element base (9) and the cover (10) are connected to each other by a connecting element (13) such that the cover (10) is displaceable relative to the mounting element base (9), and the mounting element base (9) and the cover (10) are therefore lockable to each other by means of the at least one clip closure (23, 24) and the at least one counterpart (28, 29) and can also be opened again.

21 Claims, 7 Drawing Sheets

(58) Field of Classification Search
CPC ........ A61B 2562/221; A61B 2562/225; A61B 5/0002; A61B 5/0522; A61B 5/274; A61B 5/6833
See application file for complete search history.

(56) References Cited

U.S. PATENT DOCUMENTS

| | | | |
|---|---|---|---|
| 2008/0065111 A1* | 3/2008 | Blumenkranz | B25J 15/0009 606/130 |
| 2009/0078846 A1* | 3/2009 | Isebrand | B64D 29/06 248/542 |
| 2009/0318793 A1* | 12/2009 | Datta | A61B 5/6833 600/391 |
| 2009/0318796 A1* | 12/2009 | Datta | A61B 5/06 600/391 |
| 2013/0072870 A1 | 3/2013 | Heppe et al. | |
| 2015/0164598 A1* | 6/2015 | Blumenkranz | B25J 15/0009 606/130 |
| 2016/0302725 A1 | 10/2016 | Schultz et al. | |
| 2019/0336228 A1* | 11/2019 | Blumenkranz | A61B 34/71 |

* cited by examiner

SURFACE ELECTRODE HAVING A MOUNTING ELEMENT FOR A MAGNETIC SENSOR

RELATED DOCUMENTS

This application claims priority to German Patent Application No. 10 2018 115 812.2, filed Jun. 29, 2018, and titled SURFACE ELECTRODE HAVING A MOUNTING ELEMENT FOR A MAGNETIC SENSOR, of which IS incorporated by reference in its entirety herein.

BACKGROUND

The invention relates to a mounting element for removably receiving a sensor for transferring and/or receiving electrical currents and/or signals from the surface of the skin of an organism or from an object in the body of an organism, and to a sensor arrangement for use in a system for ascertaining a body in an organism, according to the preamble of claim 1 and the preamble of claims 16 and 21.

The invention relates to what are known as reference patches, that is, a type of disposable patch for using reusable sensor arrangements for use in systems for ascertaining, particularly locating, a body in an organism, particularly in a human body, and for ascertaining a change in the position of an organism, particularly of a person, for example during a medical exam or operation. Reference patches comprise surface electrodes having a mounting element for reusable sensors to be placed in said mounting element for use in such a system. Reference patches are thus typically intended for a single use, while the sensors received therein and connected to a system for ascertaining a body in an organism, that is, typically to an information and imaging system, are intended for multiple uses.

Sensors in the sense of the present invention are particularly reference sensors. However, said sensors are not limited to reference sensors. Reference sensors are medical products for transferring electrical currents and/or for transferring other signals, particularly from the surface of the skin of an organism, particularly of a human body.

Reference patches are typically made of a conductive electrode material, a self-adhesive bonding gel, an insulator, and an electrical connector.

The use of reference sensors is particularly provided in electrophysiology in order to enable ascertaining the 3D position of medical products, such as catheters, during an electrophysiology exam, together with an information and imaging system, particularly in the embodiment of an analysis unit.

To this end, reference sensors are attached to the uninjured skin of a patient by means of reference patches. Said sensors are thereby used for conducting through the patient and/or receiving electrical currents and/or signals originating directly or indirectly from a medical product in the patient. Physically, this can occur in various ways, such as by measuring and ascertaining the strength of a magnetic field relating to the medical product or the position of the body.

One significant field of use for ascertaining and navigating D-position is cardiac diagnostic and ablation catheters. The reference sensors enable non-fluoroscopic navigation of such medical products, particularly catheters, or perhaps detecting a change in position of the body of the patient during a medical exam or operation.

Various reference patches having surface electrodes are known in the prior art for use as disposable products in a device mapping system for displaying the localization of a device in the body of a patient. Associated patch and sensor arrangements for use in such a device mapping system are also known. As an example of such systems, reference is made to the European patent applications EP 2 389 860 A1 and EP 2 520 223 A1. These show disposable patch arrangements comprising an adhesive layer by means of which the patch arrangement can adhere to the body of the patient, an electrode layer, a foam layer disposed on the electrode layer, and what is known as an engaging element for releasably engaging a segment of a housing of a reusable sensor arrangement; the adhesive layer is a hydrogel layer; the electrode layer is disposed on the adhesive hydrogel layer; and a foam layer is further provided and comprises a plurality of recesses for receiving a sensor cable of the reusable sensor cable arrangement. The construction of a disposable patch described in said publications is shown graphically in FIGS. 7 and 8. Such disposable patches for receiving a reusable sensor arrangement for use in systems for locating and imaging medical devices are also used in the course of business. Said reference patches have a push-in mounting element by means of which the magnetic sensor is mounted during engagement; a foam pad for damping is further provided around said sensor.

In practice, however, disadvantages are associated with said technical solution.

In the known solution, said magnetic field sensor is retained in the push-in mounting element by a second retaining element. When the cable exerts tension on the magnetic field sensor at a certain angle range, the second retaining element has no effect. The sensor element can thus also be released from the push-in mounting element. A disadvantage is that the magnetic sensor can also disengage from the mounting element when the patient or the cable of the magnetic sensor moves even slightly, and the sedated and prepared patient may need to be additionally moved to renew the contact of the magnetic sensor. It is further disadvantageous that the additional foam pad having the embossed structure comprising a plurality of recesses causes additional artifacts and interfering image overlays on the imaging system, particularly X-ray exams.

Starting with said disadvantages of the prior art, the present invention relates to the technical problem, that is, the object, of providing reference patches having a surface electrode and a mounting element for sensors securely avoiding said disadvantages. A further object of the invention is to provide said reference patches inexpensively as a disposable product for hygienic use in diagnostic and further medical intervention measures. Such reference patches should particularly not be noticeable by the patient and easily removable.

A further particular objective is to enable secure and releasable receiving of the reference sensor in the mounting element so that even if the patient moves unexpectedly during the medical exam, secure data transfer is made possible; slipping and moving of the reference sensor in the mounting element should particularly be avoided.

Despite said secure receiving of the reference sensor in the mounting element, it should be further ensured that after the medical exam is completed, the reference sensor can be easily removed from the mounting element without damage and then the reference patches can be removed from the body of the patient.

Interfering artifacts and image overlays on the imaging system should be avoided.

A further object of the invention is to design said reference patches so as to be compatible with numerous systems present on the market for performing non-fluoroscopic position ascertaining or navigation of medical products, particularly catheters.

Said various considerations of the technical problem are achieved by means of a mounting element according to claim 1 and by means of a sensor arrangement according to claim 16 and by means of a use according to claim 21. Preferred embodiment examples are disclosed in the corresponding subclaims.

SUMMARY

The invention provides a mounting element as a folding mounting element for sensors, particularly magnetic sensors, and interacting with surface electrodes, wherein said mounting element forgoes an interfering foam pad. In contrast to the prior art described above, the novelty of the invention is the retaining mechanism for the sensor and the forgoing of a foam layer visually interfering under X-rays.

To the extent that the present description addresses sensors, said sensors are preferably magnetic sensors. Magnetoelastic sensors can also particularly be used. Said sensors can also comprise impulse generators.

In contrast to the described prior art, the sensor in the reference patch comprising the folding mounting element is not contacted by inserting into said mounting element, but rather, due to the design of the mounting element, by placing the sensor in a receiving space of a mounting element base and by locking the cover onto the mounting element base, whereby the sensor is securely fixed in the mounting element. After the intervention at the patient, the sensor can be removed again simply by opening the cover. The positioning of the sensor in the mounting element is ensured from the preparing of the patient for the intervention to the end of the intervention.

Such reference patches thus have the main components of an electrode, an insulator, an adhesive gel, and the mounting element, and—if the sensor has a cable connection—the connecting cable and socket. The electrodes comprise a conductive polymer infused with carbon. Said electrodes can have a diameter of 80 mm, for example, but are not limited to said size or the shape of a circle.

The back side of the electrode has a dielectric material provided as a textile and having approximately the same diameter as the electrode. The textile can be a polyester fabric or a cotton fabric. Said textile is preferably self-adhesive. Instead of a woven fabric, a knit fabric, another mesh structure, or a crocheted product. Said alternatives are also referred to as fabrics in the sense of the present invention. The fabric, however, is not a foam.

A mounting element made of plastic for receiving the magnetic sensor is present at the top of the dielectric material. The mounting element is preferably disposed in the center. For an embodiment having a cable connection, the electrode is assembled to a cable optionally having a socket at the end thereof for receiving electrical pins. An extension cable having a particular length is connected thereto in turn. All sockets and plugs and cables are preferably protected against bending.

The adhesive gel can be a typical commercial hydrogel.

The mounting element can be made of any suitable material. A plastic in the form of a polycarbonate is particularly well suited.

The adhesive can be any suitable commercially available adhesive.

The above arrangement is preferably disposed on a carrier film made of polyethylene, for example, and siliconized on one side.

BRIEF DESCRIPTION OF THE DRAWINGS

The invention disclosed above is further explained below using an embodiment example, whereby the invention is not limited to a configuration according to the present embodiment example. Shown are.

DETAILED DESCRIPTION

Considering the spatial construction of such reference patches from the bottom to the top, said patches could preferably be made first of the previously mentioned carrier film, made of polyethylene siliconized on one side. The hydrogel and then the electrode follow. The actual electrode comprises the hydrogel disposed on the carrier film and applied to the skin of the patient after removing the carrier film. The electrode is thus in turn disposed on the hydrogel and preferably made of a conductive polymer infused with carbon. The electrical cable is applied at the top side of the said electrode and is preferably enclosed in soft PVC; particularly a carbon-polyester fiber having a soft PVC jacket is advantageous.

The insulator is disposed on said previously mentioned overall arrangement and can be, as shown, a polyester fabric or a cotton fabric. The bottom side of said fabric is preferably self-adhesive. An adhesive or adhesive dot is applied to the top side of said fabric, on which the mounting element for receiving the (magnetic) sensor adheres.

The mounting element serves for releasably receiving a sensor. The sensor receives or transfers electrical currents and/or other signals from the surface of the skin of a patient or from an object present in the body of the organism.

The mounting element preferably comprises a mounting element base and a cover. The mounting element base and the cover are connected to each other by means of a connecting element such that the cover is displaceable, that is, hinged, relative to the mounting element base and can be fixed there by means to be described in more detail.

In an initial, opened state, the cover and the mounting element base are thus in a horizontal plane.

The mounting element is preferably implemented from a single material. It is further advantageous if the mounting element is implemented as a single piece.

The mounting element base and the cover can thereby comprise approximately the same base area. In the open state, said parts are connected to each other by a connecting element connecting one end face each of the mounting element base and the cover.

The connecting element disposed distally to the floor of the mounting element base can thereby be a conventional integral hinge. However, any other connector structure joined with a hinge is also possible. Implementation as a strap hinge is advantageous, wherein a flexible, thin-walled hinge relay is present between the two parts to be connected, that is, the cover and the mounting element base. The connecting element is selected so as to have the required high bending fatigue strength.

It is further possible to implement the connecting element as a snap hinge, for example, wherein two stable end positions are made possible, namely the open and the closed state of the cover and mounting element base.

The mounting element base comprises the actual receiving space for receiving the sensor. Said receiving space is formed by a floor of the mounting element base, starting from which a wall bounding the receiving space is disposed. The wall is constructed, under consideration of the typical geometric embodiment of such sensors, so as to have at least three sides disposed approximately in a U-shape relative to each other. The sides can be connected to each other by means of corners in said U-shape. The wall can also, however, be made of three side parts not connected to each other, wherein thus the corner connections to each other is missing.

For a rectangular or square base shape of the receiving space, the fourth side has an opening described in greater detail below. Said opening serves for receiving the cable of the sensor by means of which said sensor is connected to the information and imaging system. Said opening can further be implemented for receiving a protective cable sheath (bending protection).

Other than the wall and the floor of the mounting element base described above, the receiving space for receiving the sensor is open to the top, because, as is explained in greater detail below, the sensor cannot be inserted through the opening at the one side of the wall, but rather must be placed in the receiving space from above.

Said opening at the one side of the wall is bounded in width by at least one tab. Two tabs are preferably present and extend from the two open end faces of the U-shaped wall. The at least one tab or the two tabs are implemented so as to shorten the distance between the two opposite legs of the U-shaped wall. To this end, said tabs are preferably implemented as right-angled attached parts, wherein one leg of the at least one tab protrudes proximally. When two tabs are used, the opening is thereby narrowed and could be described as having a bottleneck shape.

Said U-shaped receiving space having such a bottleneck-shaped narrowing further comprises at least one clip closure, for example implemented as a lug or detent hook or the like. Said clip closure is preferably disposed at the proximal end of the U-shaped wall, preferably on the upper end face of the wall or on the upper end face of the at least one tab.

Said clip closure interacts with the counterpart thereof disposed on the inner side of the cover for closing the mounting element and allowing re-opening of the mounting element.

Corresponding to the receiving space implemented in the mounting element base by the wall and the floor, the mounting element further comprises a cover for closing and re-opening the mounting element base. A wall disposed on at least three sides is provided on the inner side of the cover, the end face (the top, horizontal face in the unfolded state) of which is implemented for contacting the corresponding top, horizontal end face of the wall of the mounting element base.

By folding over the cover onto the mounting element base and adjoining the corresponding end faces of the U-shaped wall of the mounting element base and the end face of the U-shaped wall of the cover, a closed space is produced, with the exception of the opening at the one side of both walls, for fully enclosing the sensor. Only the cable or bend protection for the cable of the sensor exits the arrangement through the opening at the open side of the U-shaped embodiment of the walls.

At least one counterpart to the at least one clip closure of the wall of the mounting element base is disposed at the end face of the wall disposed at the inner side of the cover. The arrangement is preferably such that when the cover is folded over and when the cover is locked to the mounting element base of the mounting element, the at least one counterpart engages over the at least one clip closure of the wall of the mounting element base.

The mounting element base and the cover are therefore lockable to each other by means of the at least one clip closure and the at least one counterpart to the clip closure and can also be opened again. The clip closure and the counterpart cause an audible clicking sound when closing the cover and the mounting element base.

The opening for receiving a sensor cable or a protective cable sheath (bend protection) of the sensor is disposed at the proximal side of the mounting element base. Proximal thereby refers to the side of the mounting element at which the sensor cable is received. The bottleneck-shaped narrowing of the opening of the wall of the mounting element base is implemented such that the sensor can be disposed in the receiving space only by placing, that is, lateral or diagonal inserting of the sensor through the opening is not intended, as this could lead to unintentionally pulling the sensor out of the receiving space of the mounting element base, which should be avoided.

The at least one clip closure is preferably disposed at the top end face of the wall or the top end face of the tab and is axially or radially spaced apart therefrom.

The same applies to the at least one mirror-image counterpart axially or radially spaced apart from the top end face of the wall of the cover and preferably engaging over the clip closure of the wall of the mounting element base when closing the cover.

The at least one clip closure of the wall of the mounting element base and/or the previously mentioned counterpart on the cover side can comprise a radius to prevent stress concentrations when locking and/or opening the cover.

In a preferred embodiment, the top, horizontal end face of the wall comprises a recess. It is thereby possible for the end face of the wall of the inner side of the cover to make contact with the top end face of the recess of the wall of the mounting element base when closing the cover. A sealed closing, protected against lateral shifting, of the receiving space is thereby made possible and the sensor to be received in said receiving space is protected against influences acting laterally on the mounting element or on the cover.

The floor of the mounting element base and/or the cover of the mounting element preferably comprise at least one edge region facing radially outward across the contact face of the wall. A regional overhang of the cover plate and/or of the floor beyond the receiving space defined for the sensor by the two walls is thereby produced. The closing and opening of the mounting element to be performed manually are thereby facilitated.

The plate of the cover preferably comprises a cutout for receiving a displaceable tongue. The displaceable tongue is thereby spring-loaded. In a further particularly advantageous embodiment, the tongue comprises a thicker part, such as a bulge, facing inward in the closed state of the mounting element. Said bulge contacts the top side of the sensor in the closed state of the mounting element, so that the sensor is also sufficiently protected against vertical displacements in the closed mounting element. The displaceable implementation of the tongue causes a somewhat soft pressure to be exerted on the top side of the sensor, so that both a slight clearance of motion remains for the tongue and thereby an accurate fit of the seating of the sensor in the receiving space is made possible and can also compensate for any production tolerances of the housing of the sensor to be received.

It is further advantageous if the cover comprises a recess at the proximal end of the mounting element in the closed state thereof. Certain compensatory motions of the sensor cable or the protective cable sheath (bend protection) of the cable are thereby made possible, as is desirable depending on the localization of the arrangement of the surface electrodes on the skin of the patient by means of the above-mentioned mounting element. Because said recess is present only in the cover, this means that when such a compensatory motion of the sensor cable or the protective cable sheath (bend protection) of the sensor cable presses the sensor against the floor of the mounting element base, so that even in the case of such a compensatory motion the contact of the sensor in the reference patch is maintained, and the contact of the magnetic sensor to the electrode is continuously ensured in any state of application.

From the entire description above, it is preferable that the mounting element and the surface electrode are implemented as disposable products intended for a single use.

In addition to the embodiment according to the invention of the mounting element described above, the invention relates to a sensor arrangement suitable and intended for use in a system for ascertaining a body in an organism, and comprising a mounting element as described above, an adhesive arrangement, an insulator made of polystyrene fabric or cotton fabric, and a reusable (reference) sensor for ascertaining and providing information about a body in an organism to an information and imaging system, an electrode, and a hydrogel.

The invention further relates to a use of the mounting element in a reference patch.

Said arrangement has a particular advantage in that said arrangement uses an insulator implemented without foam so that the artifacts and interfering image overlays mentioned above do not occur for X-ray exams, which is possible when using an additional foam pad, however.

The implementation of the sensor arrangement and the mounting element thereby enables the sensor to work wirelessly (e.g., using Bluetooth), as well as wired, with the information and imaging system.

Figure 1:
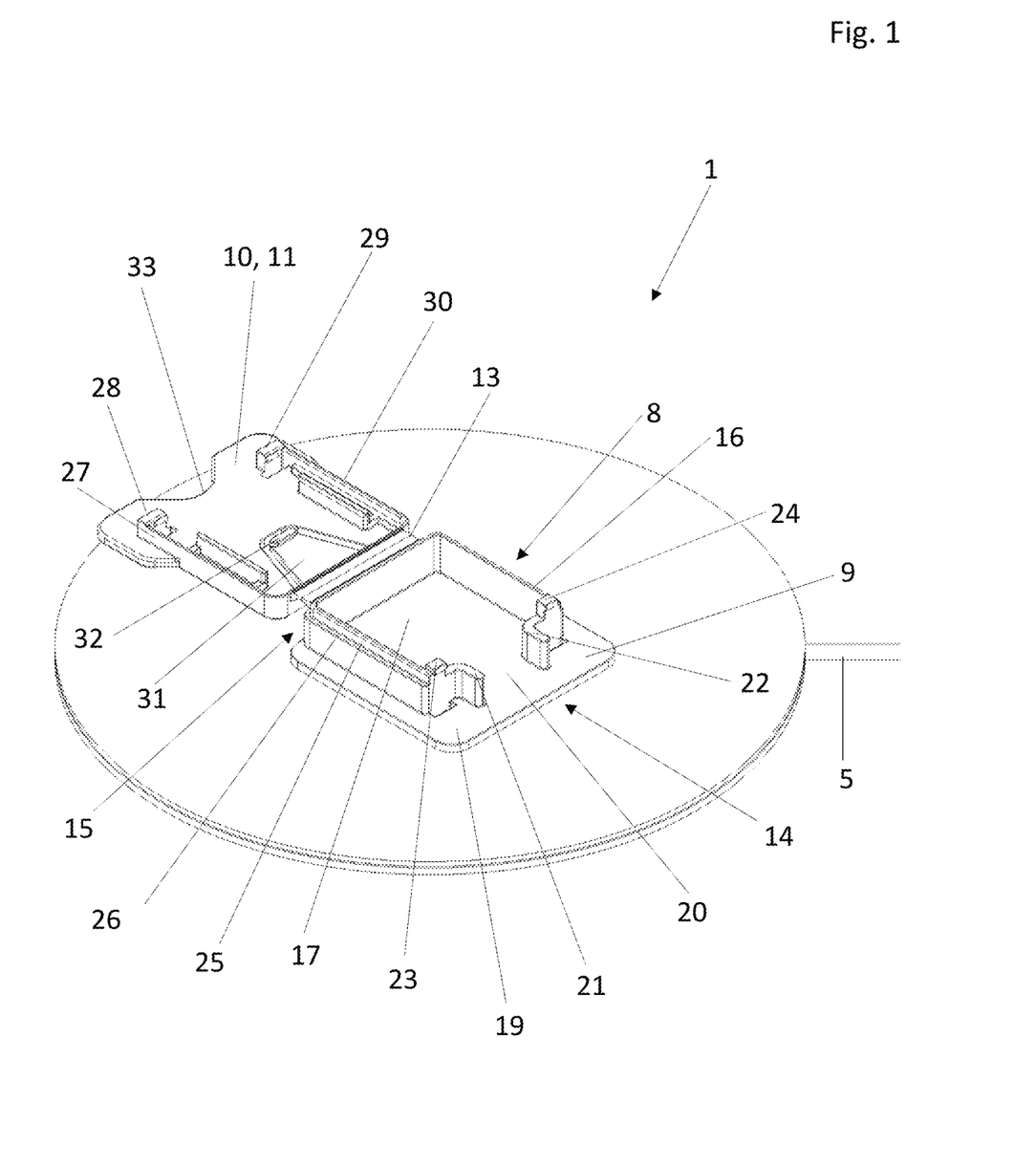
FIG. 1: an overall view of the surface electrode and open mounting element.

FIG. 1 shows the construction and arrangement of the mounting element on the surface electrode. The surface electrode is shown as a circular component. The mounting element is attached to the top side of the surface electrode shown, that is, to the insulator 6, by means of an adhesive (not shown) either as dots or covering the surface. The mounting element is shown in the open state.

Figure 2:
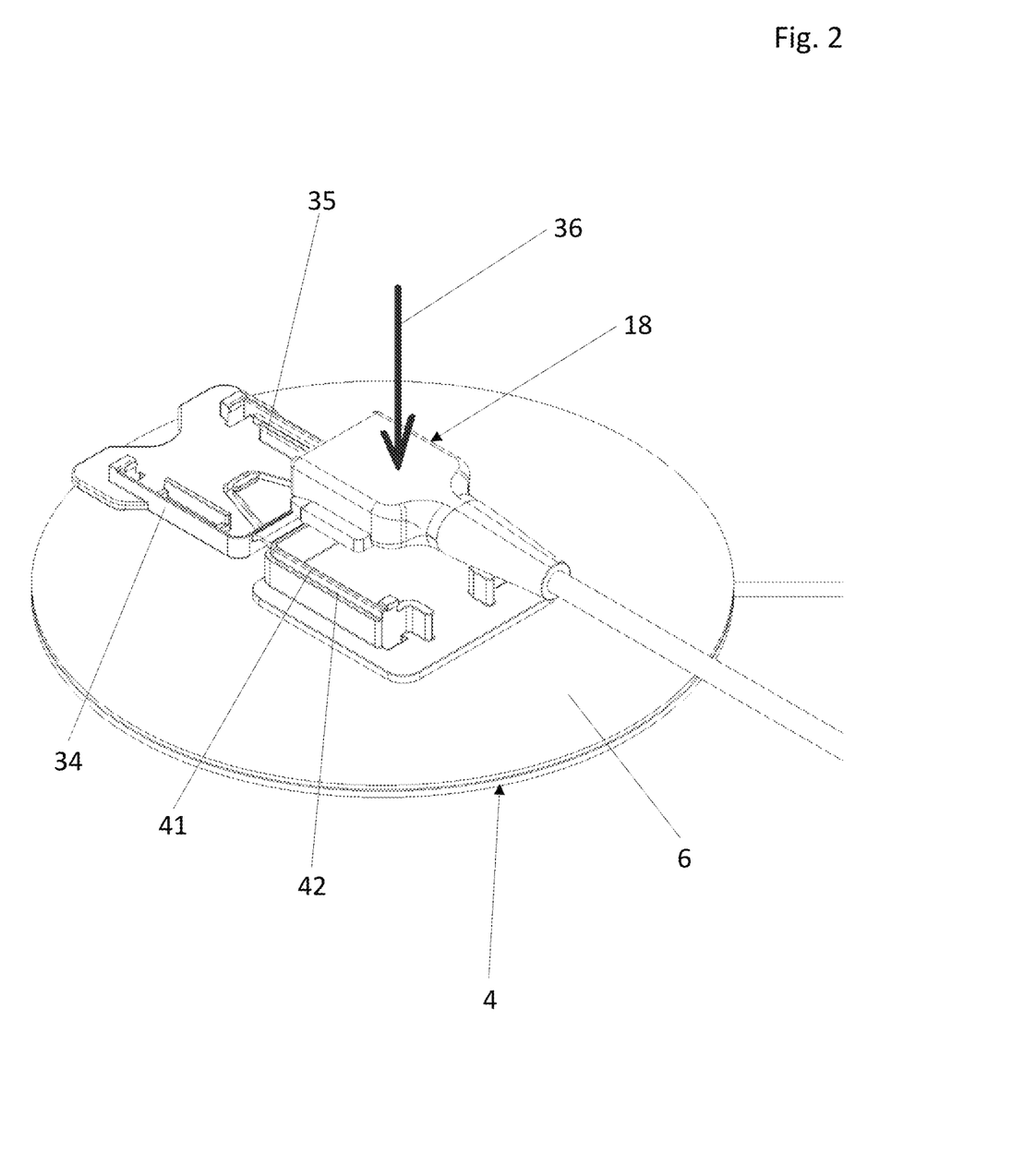
FIG. 2: a depiction of placing the sensor in the mounting element.
Figure 3:
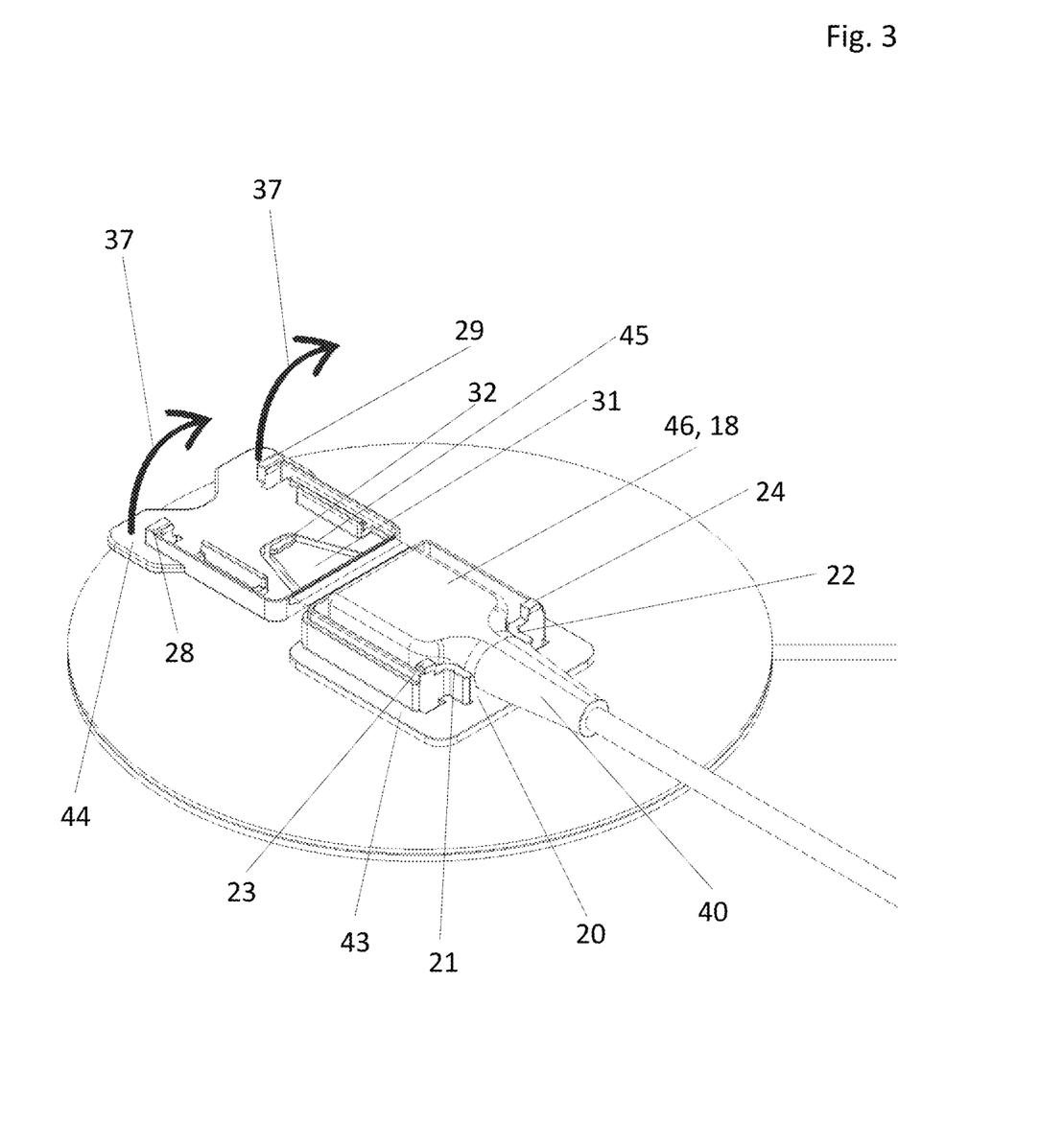
FIG. 3: a depiction of the closing motion of the cover for securing the sensor placed in the mounting element base.

According to FIG. 1, said mounting element comprises a mounting element base 9 having a receiving space 17 for receiving the sensor 18 shown in FIG. 2, FIG. 3. According to FIG. 1, the receiving space 17 is formed of a flat floor 19 forming the basis for a wall 16 disposed thereon and comprising at least three sides 16. The wall 16 is thereby U-shaped, that is, the wall 16 and therefore the receiving space 17 are not closed at the proximal end 14 of the mounting element 8. In the three-sided arrangement of the wall, the sides of the wall 16 are each joined to each other at the corners thereof, but it would also be possible if open corners were present in this respect.

FIG. 1 shows that the opening 20 of the receiving space 17 is formed by two tabs 21, 22. Said tabs are disposed on the proximal, vertical end faces of the wall 16 and have a shape running at an angle, such that the opening 20 is narrowed in comparison with a parallel course of the wall sides. Said narrowing can be referred to as a bottleneck-shaped narrowing. The narrowed opening 20 at the proximal side 14 of the mounting element base 9 serves for receiving the sensor cable 5 or the protective cable sheath 40 of the sensor 18, as is clearly shown in FIG. 3. The embodiment shown there shows that the narrowed spacing of the opening 20 produced by the tabs 21, 22 is implemented such that a bend protection grommet of the cable, in particular, is guided with a good fit. Because the tabs 21, 22 cause a longitudinal lengthening of the receiving space 17, and thus the wall 16 is elongated in said region, improved guiding of the cable 5 or the protective cable sheath 40 occurs, which is advantageous for contacting the sensor in the reference electrode. Said elongation of the receiving space in the direction of the proximal end of the mounting element is thus made possible by the locating fixing beyond the stabilization already present from the protective cable sheath 40.

The present embodiment of the receiving space according to FIG. 1, FIG. 2, and FIG. 3 shows that the sensor 18 cannot be inserted laterally into the receiving space 17 through the opening 20, but rather is placed in the open receiving space 17 from above, as expressed by the arrow 36 in FIG. 2. The sensor 18 is accordingly also secured against being pulled out unintentionally from the closed mounting element by passing through the opening 20, as can be seen in FIGS. 3 and 4.

It can be further seen in FIG. 1 and FIG. 2 that the wall 16 comprises a recess 25 in the top, horizontal end face 41 thereof. Said recess runs around all three sides of the wall in the present embodiment example, whereby FIG. 1 makes this clear only for the front side. Instead of a continuous, peripheral embodiment of the recess, sectional recesses can also be used. The top side of the recess 25 is labeled with reference numeral 26.

Figure 4:
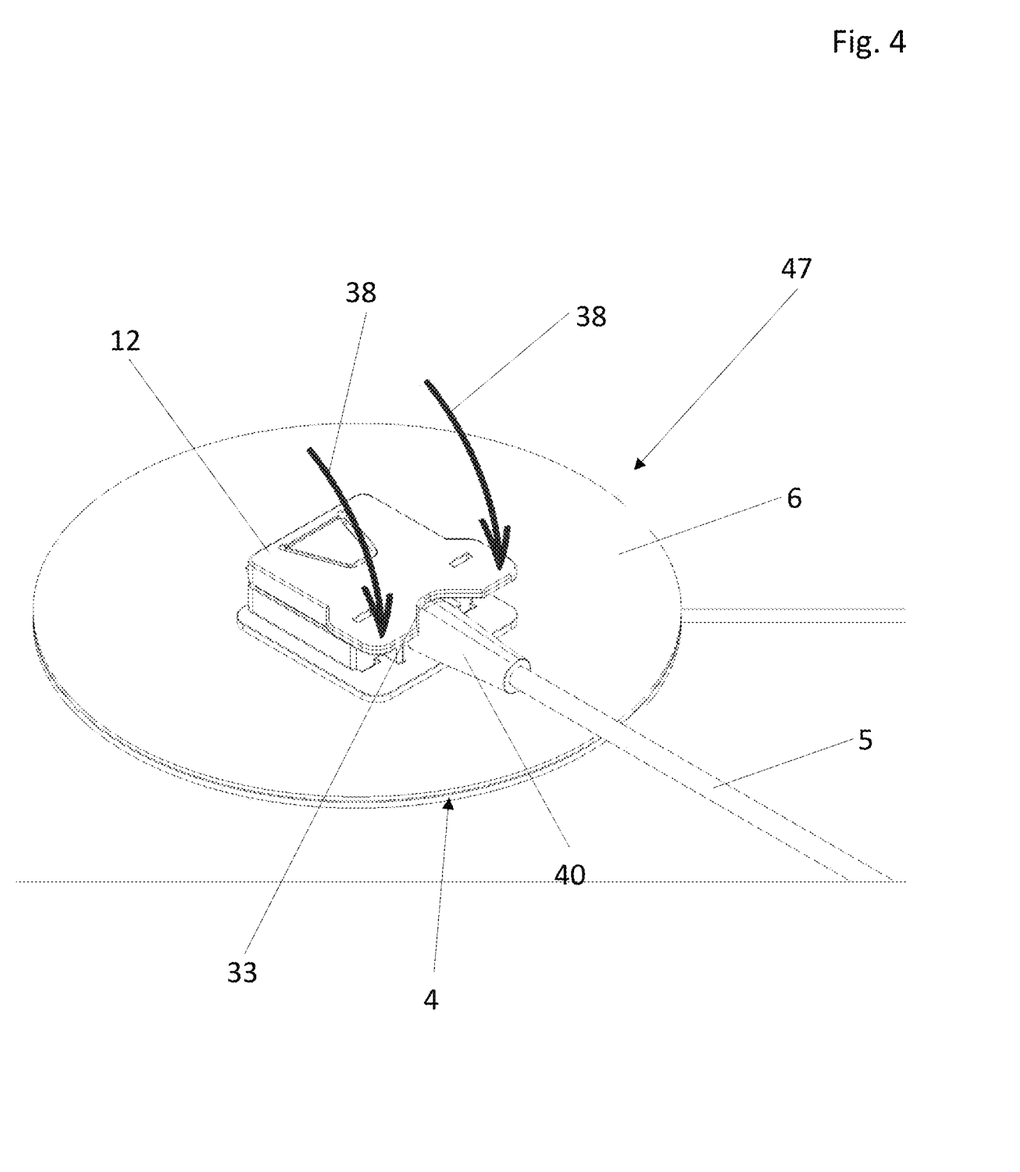
FIG. 4: a depiction of the locking motion of the cover for closing the mounting element.
Figure 5:
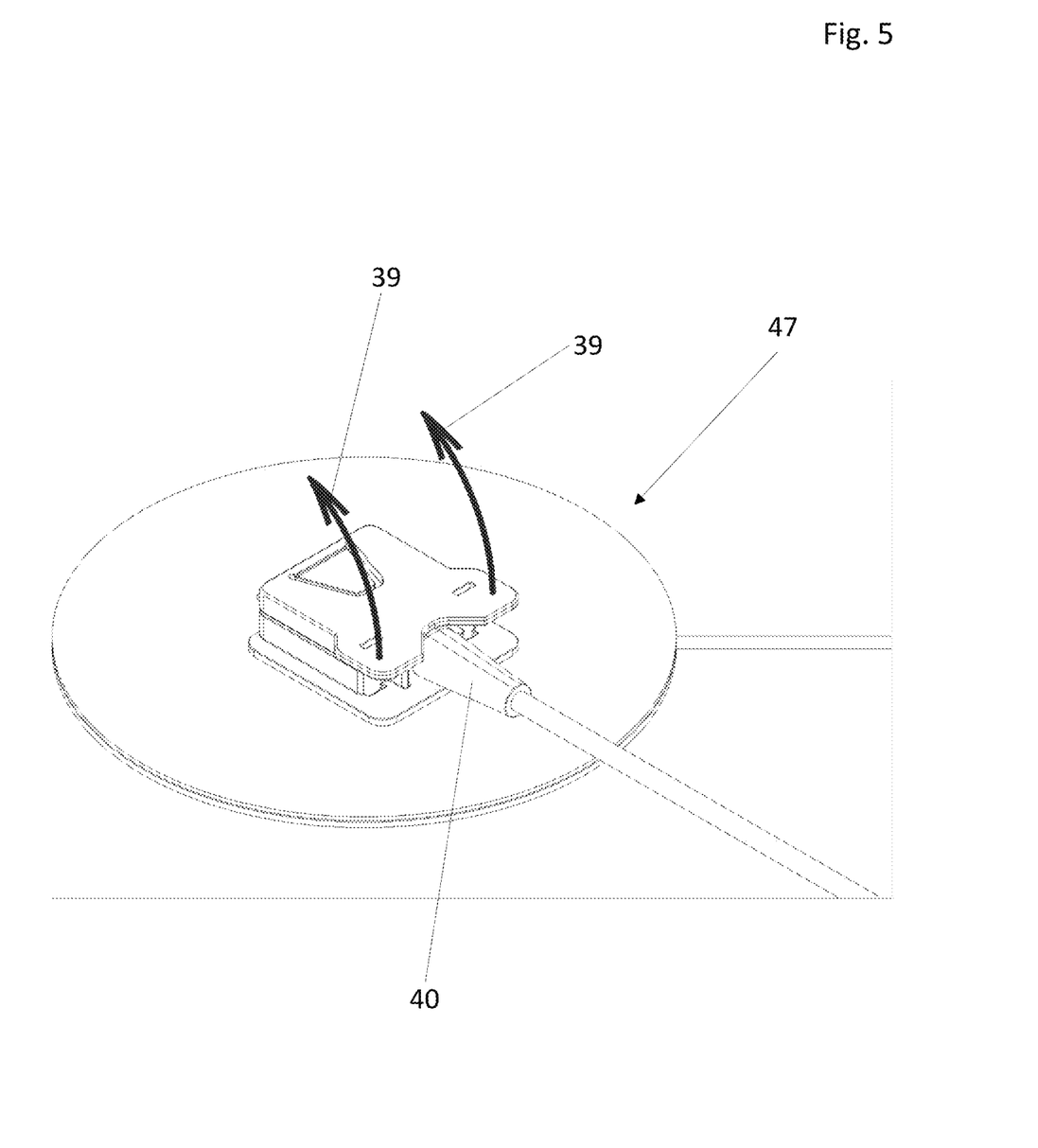
FIG. 5: a depiction of the opening motion of the over for the purpose of removing the sensor from the mounting element.

FIG. 1 further shows a cover 10 as part of the mounting element 8, covering the mounting element base 9 in the closed state shown in FIG. 3, 4, 5. A wall 27 is disposed on the inner side 11 of the cover 10, as shown in FIG. 1, for example, also disposed in a U-shape like the wall 16 of the mounting element base 9, so that when the cover 10 is closed, precisely fit contact between the corresponding top, horizontal end faces of the walls 27 and 16 is ensured. The top end face 30 of the wall 27 thereby contacts the end face 41 of the wall 16 of the mounting element base in the closed state.

In the embodiment shown in FIG. 1 and FIG. 2, for example, the contact of the wall 27 thereby occurs in such a manner that the end face 30 of the wall 27 of the inner side 11 of the cover 10 contacts the top end face 42 of the recess 25 of the wall 16 of the mounting element base 9 when the cover 10 is locked.

As is shown in FIG. 1 and FIG. 3, for example, clip closures 23, 24 are disposed at the proximal end of the wall 16 and are axially spaced apart from the top end face of the wall 16 and thereby comprise a lug-like protrusion (not shown) facing in the direction of the proximal end of the mounting element. Said clip closures 23 and 24 interact with corresponding counterparts 28 and 29 on the side of the cover also latching at the proximal end of the cover by means of the clip closures 23 and 24 in the closed state of the mounting element. To this end, the counterparts 28 and 29 in the present embodiment example are also at the height of the wall 27. Said counterparts are thereby disposed at the proximal end faces of the parallel wall surfaces 27.

The mounting element base 9 and the cover are connected to each other by a connecting element 13 disposed at the distal end 15 of the mounting element base 9, such that the cover 10 can be displaced relative to the mounting element base 9 and the mounting element base 9 and the cover 10 can be locked relative to each other by means of the two clip closures 23 and 24 and the two counterparts 28 and 29 and can be opened again from the closed state. The connecting element in the present embodiment is implemented as an integral hinge.

FIGS. 1 and 3 show, for example, that the floor 19 of the mounting element base forms an edge region 43 at least in regions facing radially outward or protruding beyond the contact surface of the wall 16, and an edge region 44 implemented at least in regions is similarly present on the cover 10 and faces radially outward across the contact surface of the wall 27. The cover arrangement can thereby be handled easily when placing the sensor, when fixing in place, and when removing the sensor.

As can be seen in FIG. 1 and FIG. 4, the surface of the cover 10 comprises a recess 33 at the proximal end of the mounting element 8 in the closed state thereof. This enables certain compensatory motions when positioning the sensor or the protective cable sheath 40, correspondingly bringing about a certain freedom of motion while performing the examination on the patients.

FIG. 2 shows fixing elements 34 and 35 running parallel to the wall 27 and bringing about a precision-fit attachment of the sensor 18 in the receiving space 17 when the cover is locked to the mounting element base 9. Arrow 36 shows the placing motion of the sensor 18 into the receiving space 17.

The arrows 37 in FIG. 3 indicate the closing motion direction of the cover 10 when the sensor 18 is placed. The figure further shows that the cover 10 comprises a cutout 45 cut into the surface of the cover in regions for receiving a displaceable tongue 31. Said tongue comprises a thick part 32 in the embodiment shown, making contact with the top side 46 of the sensor 18 in the closed state of the mounting element 8 and thereby contributing to vertically fixing the sensor in the receiving space 17, wherein the displaceable embodiment of the tongue 31 enables a certain vertical compensatory motion. A flexible, downward-directed pressure of the sensor 18 is thereby accomplished overall in the receiving space 17 so that permanent contact between the sensor and the reference electrode is ensured.

FIG. 4 shows the reference sensor 47 in the state thereof immediately prior to locking. Locking takes place by means of pressure in the direction of arrow 38 on the top side 12 of the cover 10, whereby the previously described latching procedure takes place between the clip closures 23 and 24 and the counterparts 28 and 29.

The arrows 39 in FIG. 5 indicate how the mounting element 8 is opened again by displacing the cover 10 upward from the closed state.

Figure 6:
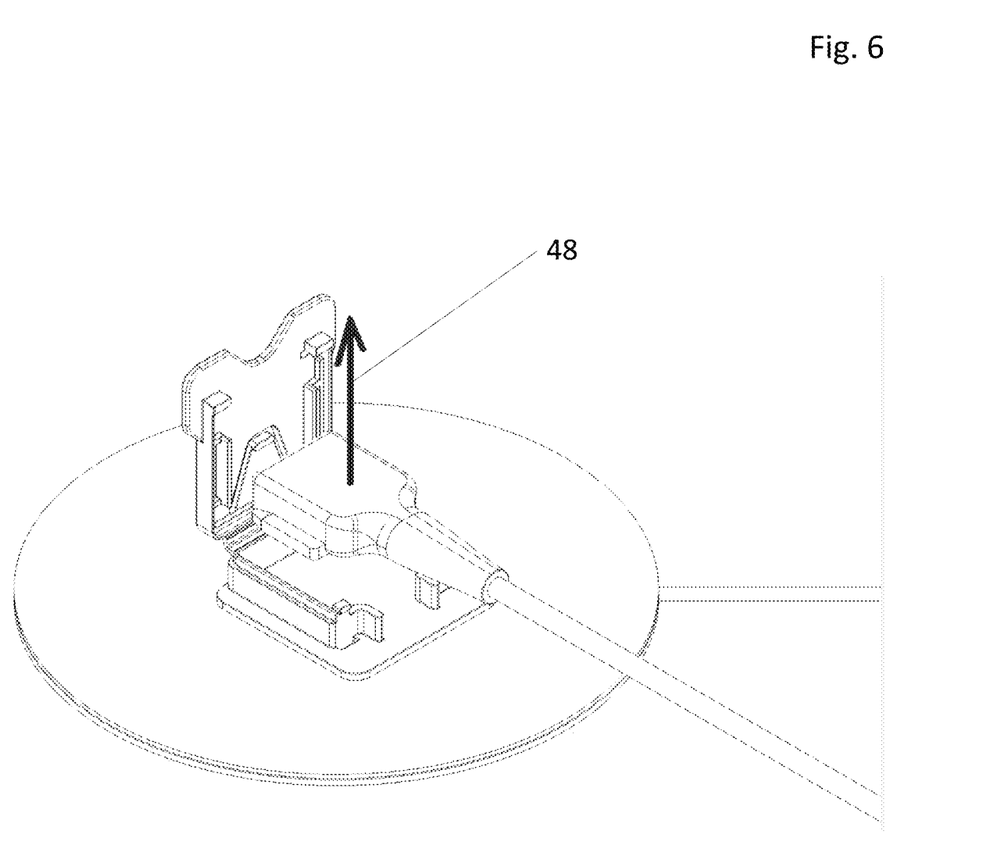
FIG. 6: the removing motion of the sensor out of the reopened mounting element.

FIG. 6 shows the motion of removing the sensor 18 from the receiving space 17 by means of the arrow 48.

Common throughout FIG. 1-FIG. 6 is that the mounting element 8 is disposed on the surface of the insulator 6. The electrode 4 disposed below the insulator 6 is indicated.

Figure 7:
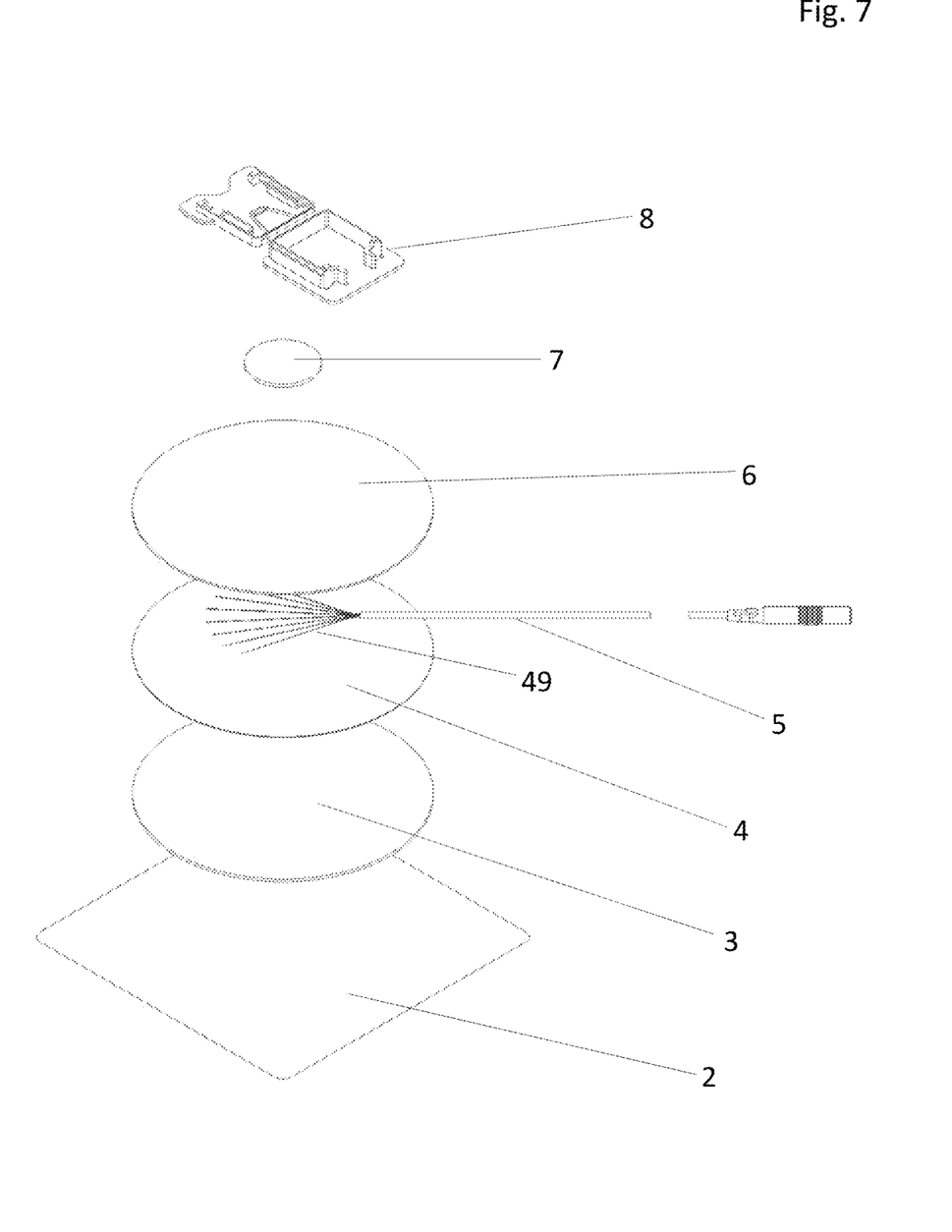
FIG. 7: the construction of the surface electrode having a mounting element for receiving the sensor.

The fundamental structure of the surface electrode and mounting element can be seen in FIG. 7. Said structure is free of foam. FIG. 7 shows a plan view of the explained mounting element 8 disposed by means of an adhesive 7 disposed on the top side of the insulator 6. The insulator 6 is thereby implemented as a (polyester or cotton) fabric. The bottom side of the insulator is self-adhesive, so that a fixed connection between the insulator 6 and the top side of the electrode 4 is thereby made possible. No foam layer is disposed between the mounting element 8 and the insulator 6. The open (copper) end 49 of the cable 5 is present there in between for bringing about the desired signals or electrical current desired by the arrangement. The bottom side of the electrode 4 is coated with a hydrogel for applying to the skin of the patient after pulling off the siliconized carrier film 2, thereby bringing about the attaching of the surface electrode and mounting element required for performing the medical exam.

A corresponding sensor arrangement 47 including the reference patch and the reusable sensor 18 can also be seen in the figures.

REFERENCE NUMERAL LIST

1 Disposable patch arrangement
2 Carrier film
3 Hydrogel
4 Electrode
5 Sensor cable
6 Insulator
7 Adhesive arrangement
8 Mounting element
9 Mounting element base for sensor
10 Cover
11 Inner side of the cover
12 Outer side of the cover
13 Connecting element
14 Proximal end of mounting element 8
15 Distal end of mounting element 8
16 Wall of mounting element base 9
17 Receiving space for the sensor
18 Sensor
19 Floor of mounting element base 9
20 Opening in the proximal end of mounting element 8
21 Tab
22 Tab
23 Clip closure
24 Clip closure
25 Recess at the end face of wall 16
26 Top side of recess 25
27 Wall of cover 10
28 Counterpart
29 Counterpart
30 End face of wall 27
31 Displaceable tongue
32 Thick part of tongue 31
33 Cutout
34 Fixing element
35 Fixing element
36 Arrow insertion direction for sensor 18
37 Arrow closing direction for cover 10
38 Arrow pressing direction for cover 10
39 Arrow opening direction for cover 10
40 Protective cable sheath
41 Top end face of wall 16
42 Top end face of recess 25
43 Edge region of floor 19
44 Edge region of inner side 11 of cover 10
45 Cutout 46 Top side of sensor 16
47 Sensor arrangement
48 Arrow removal direction for sensor
49 Open ends of cable 5

The invention claimed is:

1. A mounting element (8) for releasably receiving a sensor (18) for transferring and/or receiving electrical currents and/or signals relating to a body of an organism, comprising
   a mounting element base (9) having a receiving space (17) for receiving the sensor (18), the receiving space (17) comprising:
      a floor (19),
      a first wall (16) disposed on the floor (19) and disposed on at least three sides,
      an opening (20) formed by at least one tab (21, 22), the opening (20) disposed in the first wall (16) for receiving a sensor cable (5) or a protective cable sheath (40) of the sensor (18), disposed at the proximal side (14) of the mounting element base (9)
      at least one clip closure (23, 24), and
   a cover (10) for the mounting element base (9), the cover comprising:
      an at least three-sided second wall (27) disposed on an inner side (11) of the cover (10), and an end face (30) of the second wall being implemented for contacting an end face (41) of the first wall (16);
      wherein at least one counterpart (28, 29) to the at least one clip closure (23, 24) is disposed on the second wall (27), and
   wherein, the mounting element base (9) and the cover (10) are connected to each other by a connecting element (13) such that the cover (10) is displaceable relative to the mounting element base (9), and
   the mounting element base (9) and the cover (10) are therefore selectably lockable to each other by means of the at least one clip closure (23, 24) and the at least one counterpart (28, 29), and can also be opened again.

2. The mounting element according to claim 1, characterized in that the connecting element (13) is implemented as an integral hinge.

3. The mounting element according to claim 1, characterized in that the opening (20) is narrowed in a bottleneck shape relative to the spacing of the opposite sides of the first wall (16) by the at least one tab (21, 22) protruding from the first wall (16).

4. The mounting element according to claim 1, characterized in that the opening (20) of the first wall (16) is narrowed such that the sensor (18) can be disposed only by placing in the receiving space (17).

5. The mounting element according claim 1, characterized in that the at least one clip closure (23, 24) is axially or radially spaced apart from the top end face (41) of the first wall (16) or the tab (21, 22).

6. The mounting element according to claim 1, characterized in that the at least one clip closure (23, 24) comprises a radius for preventing stress concentrations when locking and/or opening the cover (10).

7. The mounting element according to claim 1, characterized in that the top end face (41) of the first wall (16) comprises a recess (25).

8. The mounting element according to claim 1, characterized in that the end face (30) of the second wall (27) of the inner side (11) of the cover (10) makes contact with the top end face (42) of the recess (25) of the first wall (16) of the mounting element base (9) when closing the cover (10).

9. The mounting element according to claim 1, characterized in that the floor (19) of the mounting element base (9) at least in regions comprises one edge region (43) facing radially outward across the contact face of the first wall (16).

10. The mounting element according to claim 1, characterized in that the cover (10) at least in regions comprises one edge region (44) facing radially outward across the contact face of the wall (27).

11. The mounting element according to claim 1, characterized in that the cover (10) comprises a cutout (45) for receiving a displaceable tongue (31).

12. The mounting element according to claim 11, characterized in that the displaceable tongue (31) comprises a thick part (32) facing inward in the closed state of the mounting element (8) for contacting the top side (46) of the sensor (18).

13. The mounting element according to claim 1, characterized in that the cover (10) comprises a recess (33) at the proximal end of the mounting element (8) in the closed state thereof.

14. The mounting element according to claim 1, characterized in that the mounting element is implemented as a disposable product.

15. A sensor arrangement (47), comprising:
   a mounting element (8) comprising:
      a mounting element base (9) having a receiving space (17) for receiving the sensor (18), the receiving space (17) comprising:
         a floor (19),
         a first wall (16) disposed on the floor (19) and disposed on at least three sides,
         an opening (20) formed by at least one tab (21, 22),
         at least one clip closure (23, 24), and
      a cover (10) for the mounting element base (9), the cover comprising:
         an at least three-sided second wall (27) disposed on an inner side (11) of the cover (10), and an end face (30) of the second wall being implemented for contacting an end face (41) of the first wall (16);
         wherein at least one counterpart (28, 29) to the at least one clip closure (23, 24) is disposed on the second wall (27), and
      wherein, the mounting element base (9) and the cover (10) are connected to each other by a connecting element (13) such that the cover (10) is displaceable relative to the mounting element base (9), and
      the mounting element base (9) and the cover (10) are therefore selectably lockable to each other by means of the at least one clip closure (23, 24) and the at least one counterpart (28, 29), and can also be opened again;
   a reusable sensor (18) for receiving electrical currents and/or signals with respect to a body of an organism and for transferring said electrical currents and/or signals to an information and imaging system;
   an adhesive arrangement (7);
   an insulator (6) made of a polyester fabric or cotton fabric;
   an electrode (4); and
   a hydrogel (3).

16. The sensor arrangement according to claim 15, characterized in that the electrode comprises a conductive polymer infused with carbon.

17. The sensor arrangement according to claim 15, characterized in that the sensor (18) is a magnetic sensor or a magnetoelastic sensor.

18. The sensor arrangement according to claim 15, characterized in that the sensor arrangement (47) and/or the insulator (6) are implemented free of foam.

19. The sensor arrangement according to claim 15, characterized in that the sensor (18) is connected to the information and imaging system wirelessly or by means of a cable.

20. A use of a mounting element (8) as a reference patch, the mounting patch comprising:
- a mounting element base (9) having a receiving space (17) for receiving the sensor (18), the receiving space (17) comprising:
  - a floor (19),
  - a first wall (16) disposed on the floor (19) and disposed on at least three sides,
  - an opening (20) formed by at least one tab (21, 22),
  - at least one clip closure (23, 24), and
- a cover (10) for the mounting element base (9), the cover comprising:
  - an at least three-sided second wall (27) disposed on an inner side (11) of the cover (10), and an end face (30) of the second wall being implemented for contacting an end face (41) of the first wall (16);
  - wherein at least one counterpart (28, 29) to the at least one clip closure (23, 24) is disposed on the second wall (27), and
- wherein, the mounting element base (9) and the cover (10) are connected to each other by a connecting element (13) such that the cover (10) is displaceable relative to the mounting element base (9), and
- the mounting element base (9) and the cover (10) are therefore selectably lockable to each other by means of the at least one clip closure (23, 24) and the at least one counterpart (28, 29), and can also be opened again; and the use comprising:
- an adhesive arrangement (7),
- a foam-free insulator (6) made of a synthetic fiber fabric or cotton fabric,
- an electrode (4),
- a hydrogel (3), and
- having a cable (5).

21. The use according to claim 20, characterized in that the sensor cable (5) is disposed between a bottom side of the insulator (6) and a top side of the electrode (4).

* * * * *